US005520625A

United States Patent [19]

Malewicz

[11] Patent Number: 5,520,625
[45] Date of Patent: May 28, 1996

[54] RANGE-OF-MOTION WRIST SPLINT

[75] Inventor: Andrzej Malewicz, Minneapolis, Minn.

[73] Assignee: Empi, Inc., St. Paul, Minn.

[21] Appl. No.: 388,482

[22] Filed: Feb. 14, 1995

Related U.S. Application Data

[63] Continuation-in-part of Ser. No. 205,837, Mar. 3, 1994, Pat. No. 5,437,619, which is a continuation-in-part of Ser. No. 85,758, Jun. 30, 1993, Pat. No. 5,399,154.

[51] Int. Cl.$^6$ ........................................ A61F 5/00
[52] U.S. Cl. .................... 602/21; 602/5; 602/16; 602/20; 602/23; 602/26; 623/20
[58] Field of Search ................................... 602/5, 16, 17, 602/20, 21, 23, 26, 27; 482/127; 601/27, 33, 62; 623/21, 20, 57, 61–62; 128/26, 77, 878

[56] References Cited

U.S. PATENT DOCUMENTS

| | | | |
|---|---|---|---|
| 4,809,688 | 3/1989 | del Valle et al. | 602/20 |
| 5,052,379 | 10/1991 | Airy et al. | 602/16 |
| 5,358,469 | 10/1994 | Patchel et al. | 602/5 |
| 5,399,154 | 3/1995 | Kipnis et al. | 602/26 |
| 5,437,619 | 8/1995 | Malewicz et al. | 602/20 |

*Primary Examiner*—Richard J. Apley
*Assistant Examiner*—Kim M. Lee
*Attorney, Agent, or Firm*—Kinney & Lange

[57] ABSTRACT

A range-of-motion splint for applying torque to a wrist joint of a patient is described. The range-of-motion splint is designed so that it provides for the natural motion of the wrist joint which is a three-dimensional motion including medial rotation of the hand at the wrist joint in conjunction with a flexion or extension motion of the wrist joint. The range-of-motion splint includes a palm plate for supporting a palm of the patient. First pivot means pivotally connects a hand bracket to the palm plate such that the palm plate is capable of moving laterally with respect to the hand bracket. Second pivot means pivotally connects a wrist bracket to the hand bracket. Torque applying means is connected to the hand bracket and the wrist bracket for applying torque between the hand bracket and the wrist bracket.

11 Claims, 5 Drawing Sheets

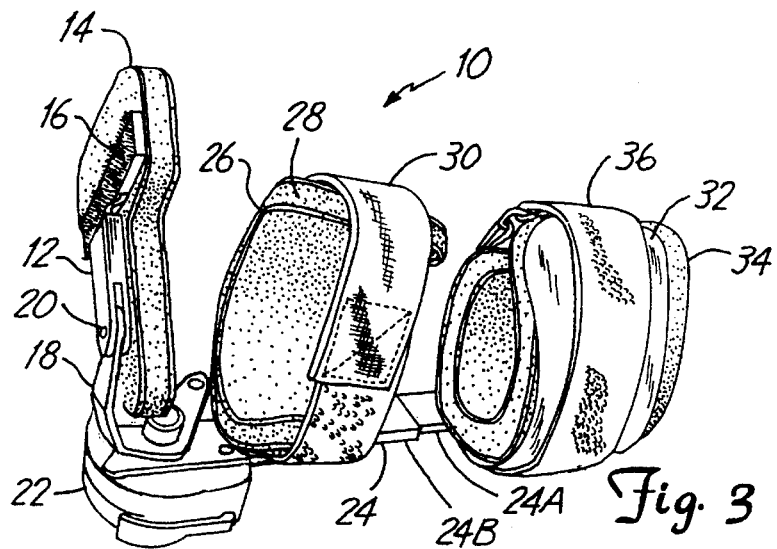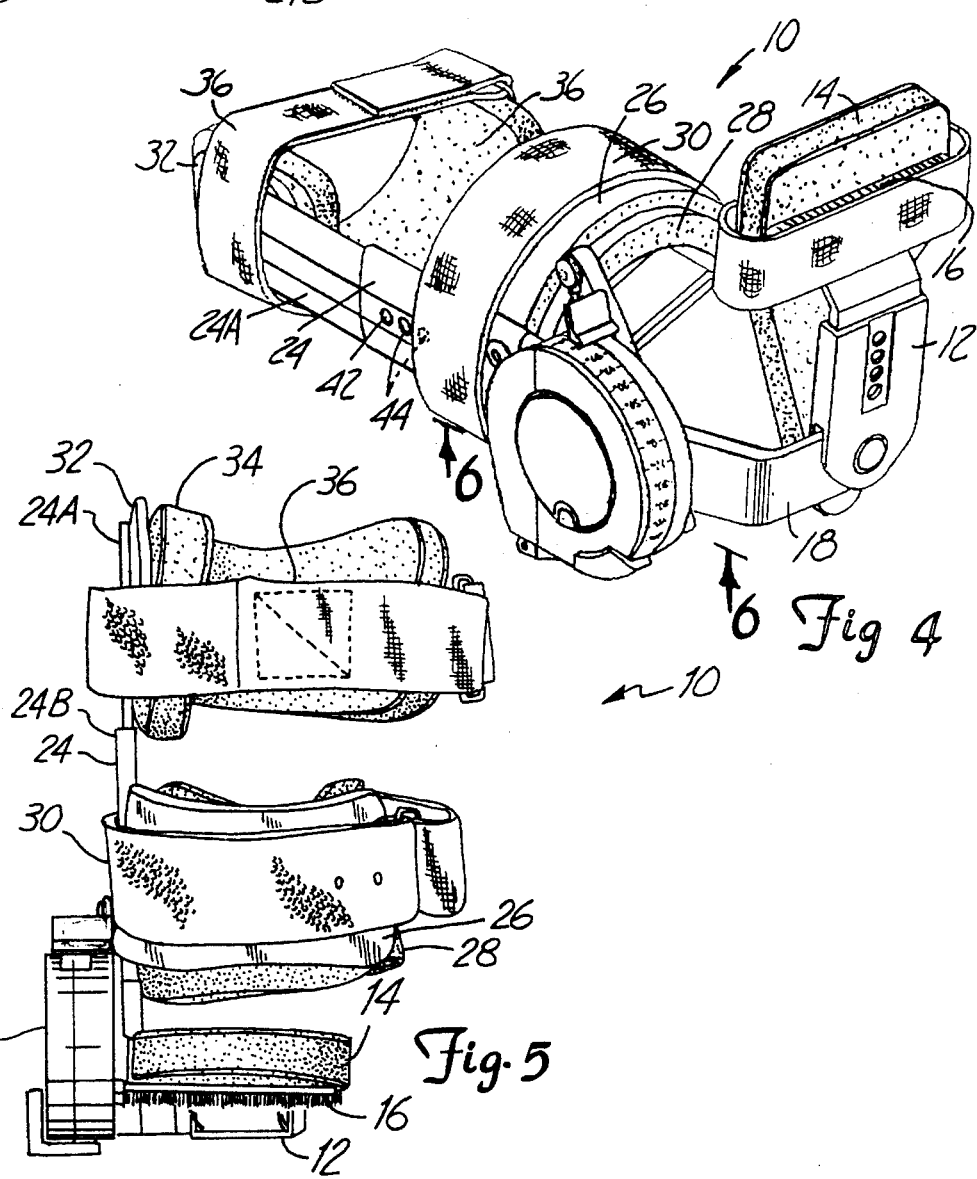

RANGE-OF-MOTION WRIST SPLINT

REFERENCE TO RELATED APPLICATIONS

This application is a continuation-in-part of commonly assigned U.S. patent application Ser. No. 08/205,837, filed Mar. 3, 1994, entitled RANGE-OF-MOTION SPLINT WITH ECCENTRIC SPRING, U.S. Pat. No. 5,437,619 which is a continuation-in-part of commonly assigned U.S. patent application Ser. No. 08/085,758, filed Jun. 30, 1993 entitled CONSTANT TORQUE RANGE-OF-MOTION SPLINT, U.S. Pat. No. 5,399,154.

Reference is made to the following commonly assigned and copending applications: U.S. patent application Ser. No. 08/382,993, filed on Feb. 3, 1995, entitled RANGE-OF-MOTION ANKLE SPLINT by Andrzej Malewicz and U.S. patent application Ser. No. 08/383,063, filed on Feb. 3, 1995, entitled HALO HOOKS FOR RANGE-OF-MOTION SPLINT by Andrzej Malewicz.

BACKGROUND OF THE INVENTION

The present invention relates generally to splint assemblies, and more particular to dynamic splints or braces for applying torque across joints undergoing rehabilitative therapy.

Injuries or surgery to twists, ankles, elbows, knees and other joints often results in flexion or extension contractures. These debilitating conditions prevent the patient from fully flexing (in the case of an extension contracture) or extending (in the case of a flexion contracture) the injured joint. Range-of-motion (ROM) splints are dynamic devices commonly used during physical rehabilitative therapy to increase the range of motion over which the patient can flex or extend the joint. Splints of this type are known, and disclosed, for example, in the Mitchell et al. patent entitled DYNAMIC EXTENSION SPLINT, U.S. Pat. No. 5,036,837.

Commercially available range-of-motion splints typically include spring loaded brace sections for applying torque to the injured joint in opposition to the contracture. This force tends to gradually increase the working range or angle of joint motion. Springs, however, are passive devices and exert decreasing amounts of force as they retract. Most range-of-motion splints, therefore, require continual adjustment to maintain a constant amount of applied torque as the patient's range of joint motion increases during therapy. These torque adjusting procedures are time consuming and inconvenient.

In addition, with respect to range-of-motion splints for a wrist joint, commercially available splints do not provide for the natural motion of the wrist joint which is a three-dimensional motion including medial rotation of the hand at the wrist joint in conjunction with a flexion or extension motion of the wrist joint. Rather, commercially available splits only provide for one-dimensional motion (flexion or extension).

It is evident that there is a continuing need for improved range-of-motion splints. In particular, there is a need for splints capable of applying relatively constant torque over the entire working wrist joint range without adjustments. The amount of torque applied by the splint should also be adjustable to suit the needs of different patients. In addition, the splint should provide for the natural motion of the wrist joint, which is a three-dimensional motion including medial rotation of the hand at the wrist joint in conjunction with a flexion or extension motion of the wrist joint.

SUMMARY OF THE INVENTION

The present invention is a range-of-motion splint for providing torque to a wrist joint of a patient undergoing rehabilitative therapy. The range-of-motion splint is designed so that it provides for the natural motion of the wrist joint which is a three-dimensional motion including medial rotation of the hand at the wrist joint in conjunction with a flexion or extension motion of the wrist joint.

The range-of-motion wrist splint :includes a palm plate for supporting a palm of a patient. First pivot means pivotally connects a hand bracket to the palm plate such that the palm plate is capable of moving laterally with respect to the hand bracket. Second pivot means pivotally connects a wrist bracket to the hand bracket. Torque applying means is connected to the hand bracket and the wrist bracket for applying torque between the hand bracket and the wrist bracket.

In one preferred embodiment, the range-of-motion wrist splint includes a palm pad connected to the palm plate, and palm securing means connected to the palm plate for securing the palm plate to a palm of the patient. The split also includes a wrist hook connected to the wrist bracket, a wrist pad connected to the wrist hook, and wrist securing means connected to the wrist hook for securing the wrist hook to the wrist of the patient. Similarly, the wrist splint includes a forearm hook connected to the wrist bracket, a forearm pad connected to the forearm hook, and forearm securing means connected to the forearm hook for securing the forearm hook to a forearm of the patient.

BRIEF DESCRIPTION OF THE DRAWINGS

FIG. 3 is a first side view of the range-of-motion splint.

FIG. 4 is a third perspective view of the range-of-motion splint.

FIG. 5 is a front view of the range-of-motion split.

DETAILED DESCRIPTION OF THE PREFERRED EMBODIMENTS

Figure 1:
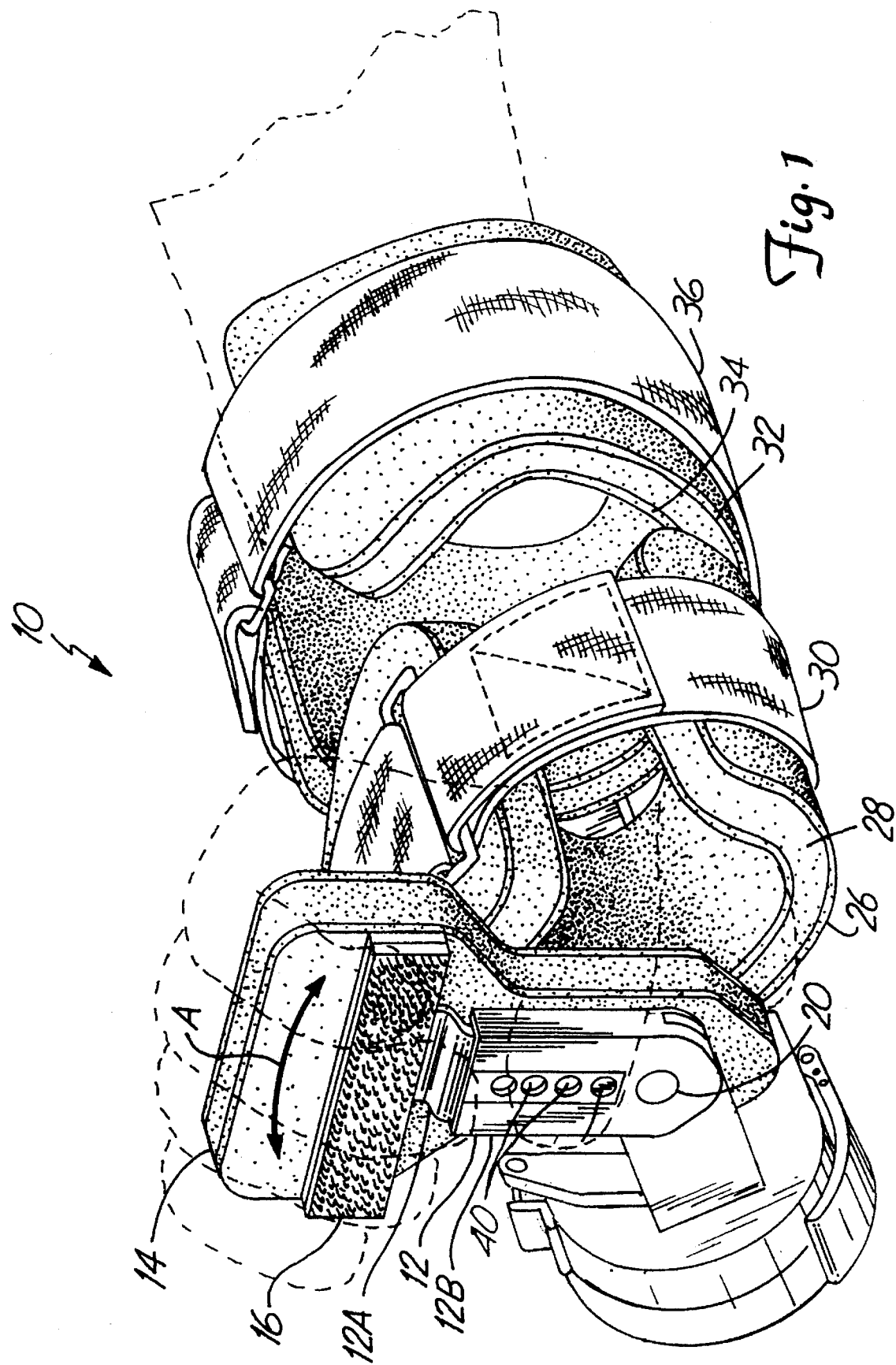
FIG. 1 is a perspective view showing a palm plate of the range-of-motion wrist splint in a first position.
Figure 2:
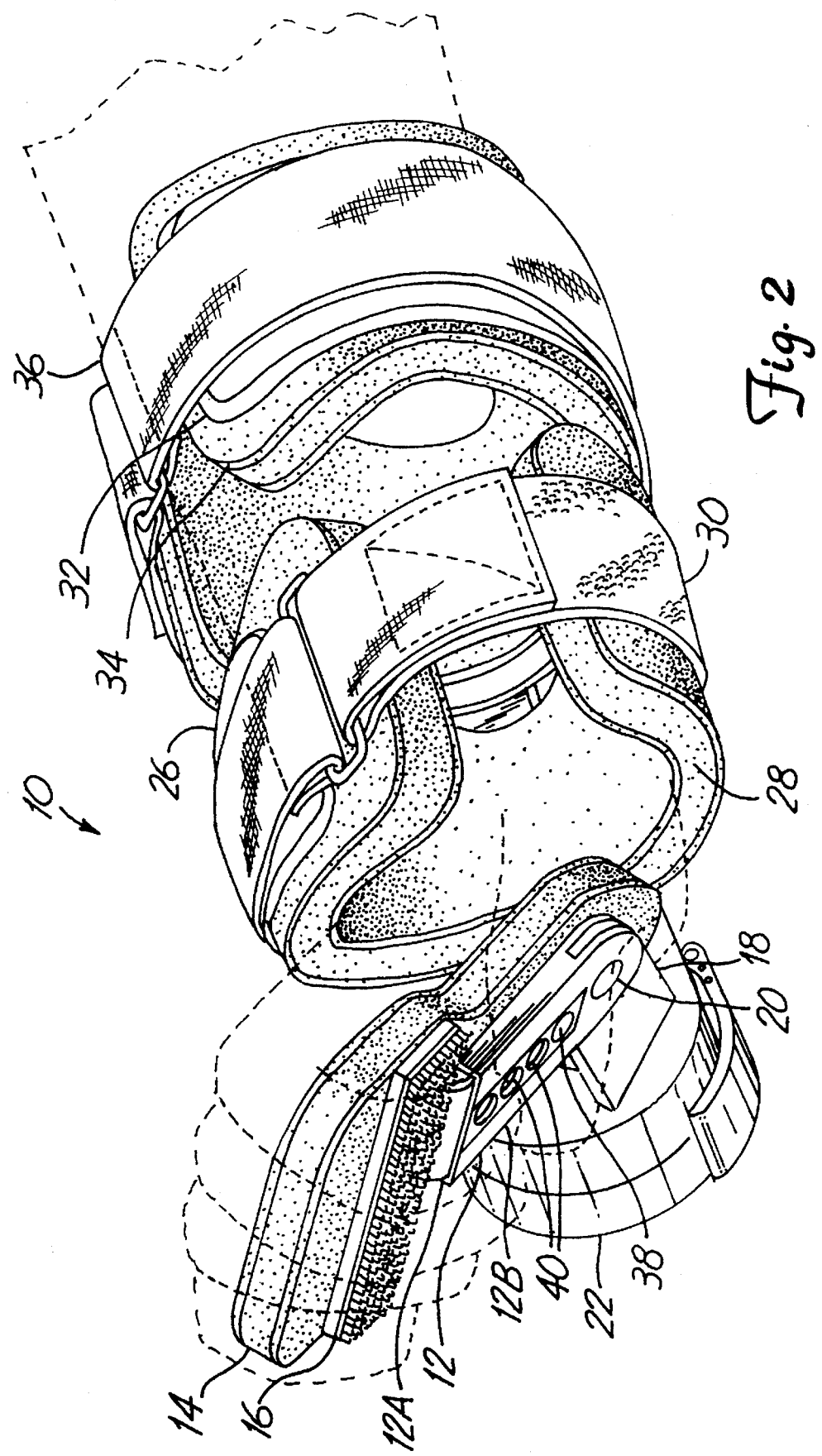
FIG. 2 is a second perspective view showing the palm plate of the range-of-motion splint in a second position.

The present invention relates to range-of-motion splint 10 shown in FIG. 1–5 for applying torque to a wrist joint of a patient. FIG. 1 is a perspective view of range-of-motion splint 10 showing palm plate 12 in a first position. FIG. 2 is a perspective view of range-of-motion splint 10 showing palm plate 12 in a second position. FIG. 3 is a first side view of range-of-motion splint 10. FIG. 4 is a perspective view of range-of-motion splint 10. FIG. 5 is a front view of range-of-motion splint 10.

As shown in FIGS. 1–5, range-of-motion splint 10 includes palm plate 12 having telescoping palm plate sections 12A and 12B, palm pad 14, palm strap 16, hand bracket 18, pivot pin 20, bias housing 22, wrist bracket 24 having first telescoping wrist bracket 24A and second telescoping wrist bracket 24B, wrist hook 26, wrist pad 28, wrist strap 30, forearm hook 32, forearm pad 34, forearm strap 36, pin 38, holes 40, pin 42 and holes 44.

In operation, a patient having a wrist joint which has undergone a flexion or extension contracture will place his hand through forearm strap 36, wrist strap 30 and palm strap 16. Wrist bracket 24 can be adjusted via pin 42 and holes 44 (shown in FIG. 4) such that forearm strap 36 and wrist strap 30 are properly positioned on the patient. Likewise, hand bracket 18 can be adjusted via pin 38 and holes 40 such that the palm of the patient can be properly positioned about palm plate 12. Palm strap 16, wrist strap 30, and forearm strap 36 can then be individually tightened to secure splint 10 to the patient. In one preferred embodiment, palm strap 16, wrist strap 30 and forearm strap 36 are formed from hook and loop materials such as materials sold under the trademark VELCRO. Range-of-motion wrist splint 10 will then be properly secured to the hand and lower arm of the patient. Palm pad 14, wrist pad 28 and forearm pad 34 prevent irritation and bruising of the patient's hand and lower arm.

Hand bracket 18 is connected to wrist bracket 24 via a pivot pin enclosed within housing 22. Housing 22 also houses a torque adjustment mechanism (shown in FIGS. 6–8) which is connected to both hand bracket 18 and wrist bracket 24 to provide torque between hand bracket 18 and wrist bracket 24.

With range-of-motion wrist splint 10 properly positioned on the patient undergoing physical rehabilitative therapy to increase the range-of-motion over which the patient can flex or extend the wrist joint, the bias means within housing 22 gradually increases the working range of angle of joint motion of the wrist. The bias means within housing 22 can be adjusted to provide the proper flexion or extension of the wrist joint.

When a patient is undergoing physical rehabilitative therapy to increase the range-of-motion over which the patient can flex or extend the wrist joint resulting from a flexion or extension contracture, the natural motion of the wrist joint is a three-dimensional motion including medial rotation of the hand at the wrist joint in conjunction with a flexion or extension motion of the wrist joint. Range-of-motion wrist splint 10 accommodates for this combined motion through the use of pivot pin 20 connecting palm plate 12 to hand bracket 18. Pivot pin 20 allows palm plate 12 to medially rotate with respect to hand bracket 18, as shown by Arrow A in FIG. 1, during a flexion or extension motion. The ability of range-of-motion wrist splint 10 to allow for medial rotation of the wrist joint in conjunction with a flexion or extension motion of the wrist joint enhances the rehabilitative process. More particularly, the proper muscles surrounding the wrist joint are properly exercised to provide a greater range of motion of the wrist joint, while improper and perhaps damaging motion of the wrist joint due to one or two dimensional movement is eliminated.

Figure 6:
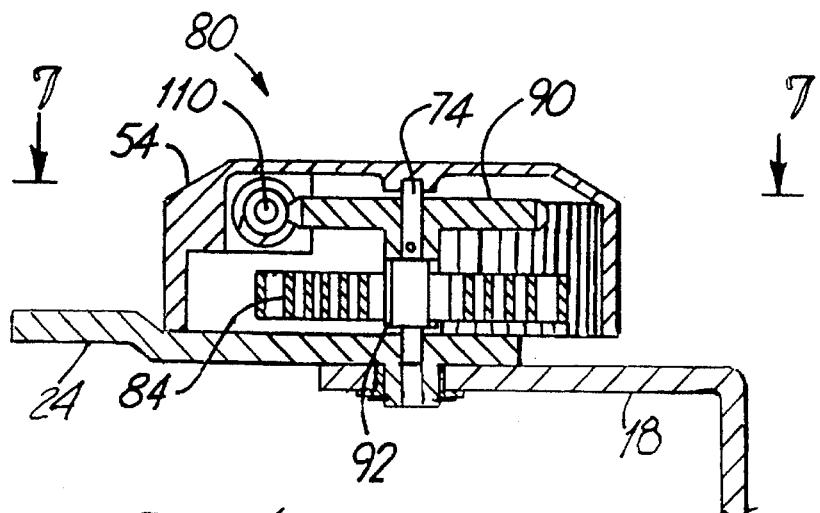
FIG. 6 is a sectional side view of the drive assembly of the present invention as shown from line 6—6 of FIG. 4.
Figure 7:
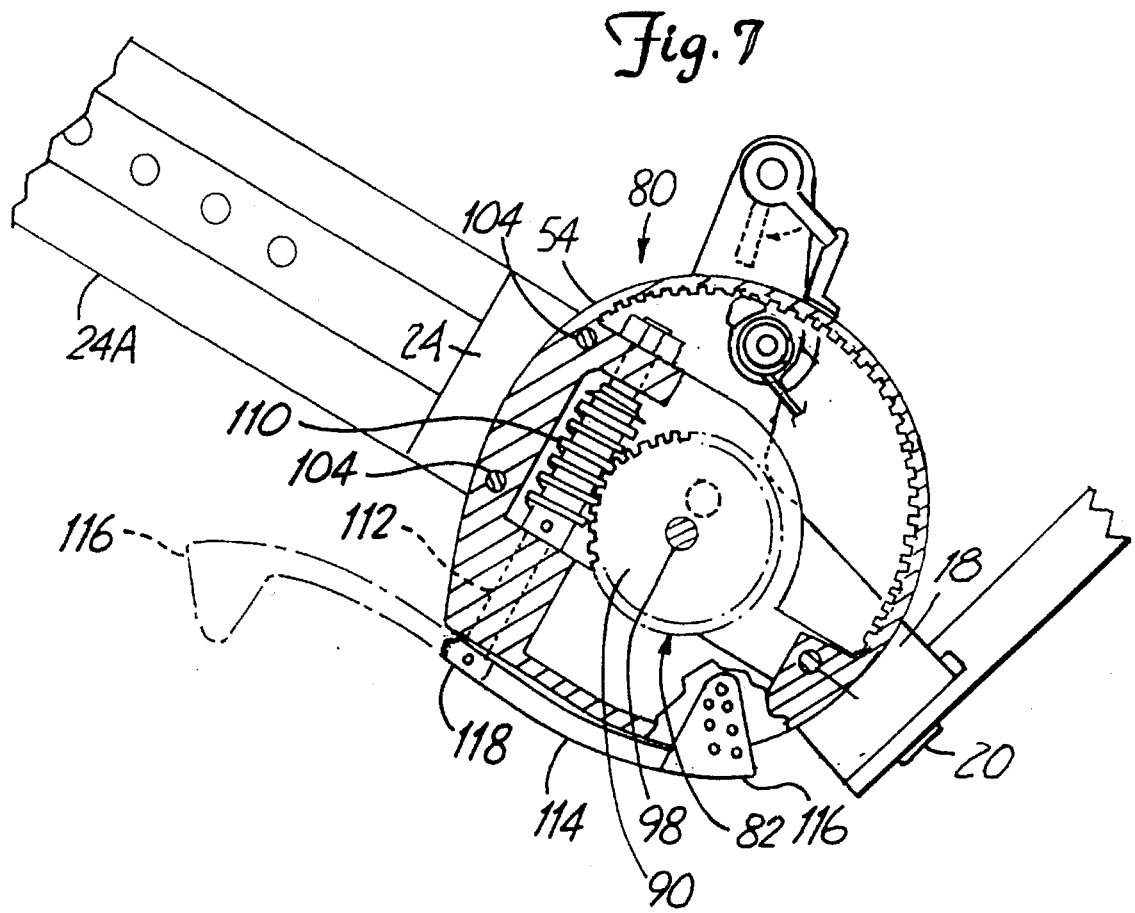
FIG. 7 is a detailed end view of the locking mechanism and the torque adjustment mechanism as shown from line 7—7 of FIG. 6, illustrating the pivot assembly.
Figure 8:
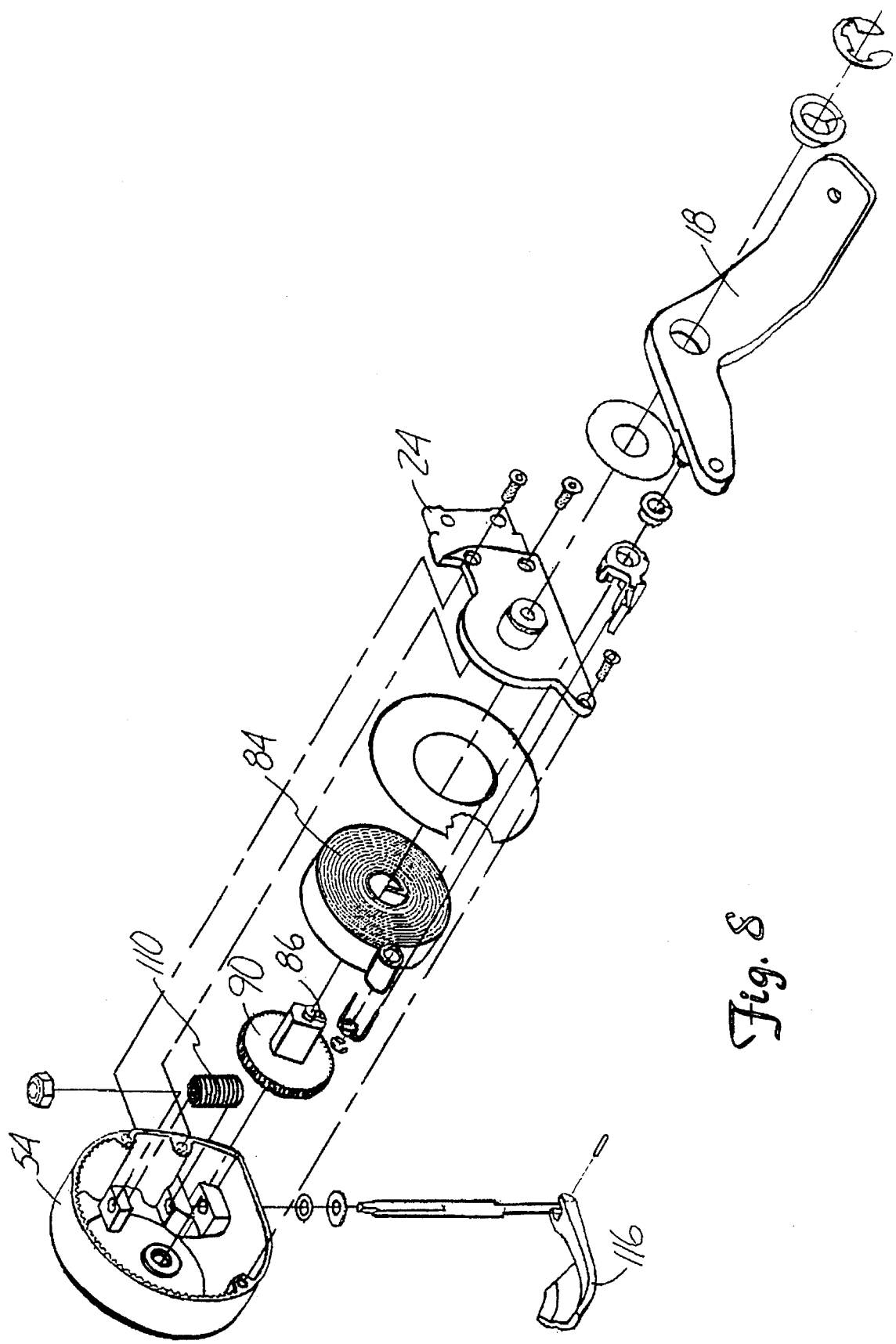
FIG. 8 is an exploded view of the drive assembly, the locking mechanism and the torque adjustment mechanism.

Drive assembly 80, which is housed in bias housing 22, is now described with reference to FIGS. 6–8. Drive assembly 80 includes protection plate 82, spiral spring 84 having inner end 86 and outer end 88, gear 90 having shaft 91 and slot 92, nut 94, adjustment worm 110 having shaft 112, crank 114 and handle 116, screws 122, bushings 124 and 126, snap fastener 128, locking mechanism 132 having holes or teeth 134, pin 136, brake 138 and switch 140.

Inner end 86 of spiral spring 84 is mounted to slot 92 within shaft 91 of gear 90. Outer end 88 of spiral spring 84 is hooked to hand bracket 18 via marker 138.

Adjustment worm 110 is mounted within housing 22 for engagement with gear 90. Shall 112 of adjustment worm 110 extends through housing 22 and is connected to crank 114 by pivot pin 118. Crank 114 is configured for pivotal movement about a retractable position adjacent housing 22 (shown in solid lines), and an extended position (shown in broken lines). When in the extended position, handle 116 of crank 114 can be actuated to rotate adjustment worm 110, thereby rotating gear 90 to wind and unwind spiral spring 84 in order to increase and decrease the amount of torque applied across wrist bracket 24 and hand bracket 18. Gear 90 and adjustment worm 110 thereby function as a torque adjustment mechanism.

Locking mechanism 132 enables wrist bracket 24 and hand bracket 18 to be conveniently and rigidly locked with respect to one another at any desired position within the range-of-motion of splint 10. Range-of-motion splint 10 is therefore configured for both flexion and extension contractures of the wrist joint. To lock range-of-motion splint 10 in a desired position, switch 140 is positioned as shorn in FIG. 7 (solid lines). In this position, switch 140 forces pin 136 to interact with holes or teeth 134, thereby locking hand bracket 18 with respect to wrist bracket 24. To unlock range-of-motion splint 10, switch 140 is moved to its position shown in FIG. 7 with hidden lines.

Range-of-motion wrist splint 10 offers considerable advantages over prior art mechanisms. The use of pivot pin 20, which connects palm plate 12 to hand bracket 18, allows range-of-motion wrist splint 10 to accommodate for the natural three dimensional motion of the wrist joint. The natural three dimensional motion including medial rotation of the hand at the wrist joint in conjunction with a flexion or extension motion of the wrist joint. Also, with the unique design of range-of-motion wrist splint 10, only a single biasing means which can be housed on the outside of the wrist joint is necessary. Thus, bulky components are not located on the inside of the wrist joint interfering with everyday activities.

Although the present invention has been described with reference to preferred embodiments, workers skilled in the art will recognize that changes may be made in form and detail without departing from the spirit and scope of the invention.

What is claimed is:

1. A range-of-motion splint for applying torque to a wrist joint of a patient, the splint comprising:

a palm plate for supporting a palm of the patient;

a hand bracket;

first pivot means for pivotally connecting the palm plate to the hand bracket such that the palm plate is capable of medial rotation with respect to the hand bracket;

a wrist bracket;

second pivot means for pivotally connecting the hand bracket to wrist bracket; and torque applying means connected to the hand bracket and the wrist bracket for applying torque between the hand bracket and the wrist bracket.

2. The splint of claim 1 and further comprising:

a wrist hook connected to the wrist bracket; and a forearm hook connected to the wrist bracket.

3. The splint of claim 2 and further comprising:

wrist securing means connected to the wrist hook for securing the wrist hook to a wrist of the patient; and forearm securing means connected to the forearm hook for securing the forearm hook to a forearm of the patient.

4. The splint of claim 3 and further comprising:

a palm pad connected to the palm plate;

a wrist pad connected to the wrist hook; and a forearm pad connected to the forearm hook.

5. The splint of claim 1 wherein the torque applying means further comprises:

a first spring-engaged mount on the wrist bracket at a position spaced from the second pivot means;

a second spring-engaged mount on the palm bracket at a position spaced from the second pivot means; and a spiral spring having an inner end and an outer end for applying torque between the wrist bracket and the hand bracket, the inner end mounted to the first spring-engaged mount and the outer end mounted to the second spring-engaged mount.

6. The splint of claim 5 and further comprising:

a torque adjustment mechanism for adjusting the torque applied by the spiral spring between the hand bracket and the wrist bracket.

7. The splint of claim 6 wherein the torque adjustment mechanism further comprises:

a gear rotatably connected to the wrist bracket at the position of the first spring-engaged mount, such that the inner end of the spring is connected to the gear; and an adjustment worm rotatably connected to the wrist bracket and engaged with the gear for rotating the gear to adjust the tension of the spiral spring.

8. The splint of claim 7 and further comprising:

a cover connected to the wrist bracket for enclosing the spiral spring and the torque adjustment mechanism; and a handle connected to the adjustment worm and capable of movement between a retracted position adjacent the cover and an expanded position, such that the handle can rotate the adjustment worm when in the extended position.

9. The splint of claim 8 and further comprising:

a locking mechanism connected to the hand bracket for releasably engaging the cover and locking the angular position of the wrist bracket with respect to the hand bracket.

10. The splint of claim 9 wherein the locking mechanism further comprises:

a rack on an interior surface of the cover;

a pawl pivotally connected to the hand bracket for releasable engagement with the rack; and a lever connected to the pawl and extending from the cover for actuating the pawl.

11. The splint of claim 1 wherein the second pivot means further provides for flexion of the hand bracket and the palm plate with respect to the wrist bracket.

* * * * *

UNITED STATES PATENT AND TRADEMARK OFFICE
CERTIFICATE OF CORRECTION

PATENT NO. : 5,520,625

DATED : MAY 28, 1996

INVENTOR(S) : ANDRZEJ MALEWICZ

Page 1 of 2

It is certified that error appears in the above-indentified patent and that said Letters Patent is hereby corrected as shown below: Title page, item [56], insert the following:

| | | | | |
|----|----|----|----|----|
| AA | 44,799 | 05/84 | SHEPARD | |
| AB | 1,847,823 | 01/32 | DRESSER | |
| AC | 1,851,241 | 03/32 | DRESSER | |
| AD | 2,395,578 | 07/43 | SVOBODA | |
| AE | 2,413,634 | 12/46 | KOLARIK | 128 80 |
| AF | 2,646,793 | 07/53 | SWIECH ET AL. | 128 80 |
| AG | 2,675,578 | 04/54 | ATWOOD ET AL. | 16 85 |
| AH | 2,797,431 | 07/57 | LORIA | 16 85 |
| AI | 2,934,785 | 05/60 | HEUER | 16 200 |
| AJ | 3,086,521 | 04/63 | DESAI ET AL. | 128 80 |
| AK | 4,180,870 | 01/80 | RADULOVIC ET AL. | 31.2 |
| AL | 4,252,111 | 02/81 | CHAO ET AL. | 128 80F |
| AM | 4,397,308 | 08/83 | HEPBURN | 128 88 |
| AN | 4,433,679 | 02/84 | MAULDIN ET AL. | 128 80F |
| AO | 4,456,002 | 06/84 | BARBER ET AL. | 128 77 |
| AP | 4,485,808 | 12/84 | HEPBURN | 128 87R |
| AQ | 4,489,718 | 12/84 | MARTIN | 128 80C |
| AR | 4,493,316 | 01/85 | REED ET AL. | 128 80C |
| AS | 4,508,111 | 04/85 | HEPBURN | 128 87R |
| AT | 4,520,804 | 06/85 | DIGEORGE | 602 26X |
| AU | 4,538,600 | 09/85 | HEPBURN | 128 88 |
| AV | 4,565,190 | 01/86 | PIRMANTGEN | 602 26 |
| AW | 4,602,620 | 07/86 | MARX | 128 77 |
| AX | 4,624,246 | 11/86 | AJEMIAN | 128 80C |
| AY | 4,633,867 | 01/87 | KAUSEK ET AL. | 128 84C |
| AZ | 4,643,177 | 02/87 | SHEPPARD ET AL. | 128 84C |
| BA | 4,657,000 | 04/87 | HEPBURN | 128 88 |
| BB | 4,719,906 | 01/88 | DEPROSPERO | 128 87A |
| BC | 4,726,361 | 02/88 | FARLEY | 128 80B |
| BD | 4,729,254 | 03/88 | NOGAMI | 744 84R |
| BE | 4,738,252 | 04/88 | FRIDDLE ET AL. | 128 80H |
| BF | 4,790,301 | 12/88 | SILFVERSKIOLD | 128 87A |
| BG | 4,817,588 | 04/89 | BLEDSOE | 128 80C |
| BH | 4,844,057 | 07/89 | HOY | 128 80C |
| BI | 4,862,878 | 05/89 | DAVISON ET AL. | 128 77 |
| BJ | 4,865,024 | 09/89 | HENSLEY ET AL. | 128 80C |
| BK | 4,873,967 | 10/89 | SUTHERLAND ET AL. | 602 26 |
| BL | 4,947,835 | 09/90 | HEPBURN ET AL. | 128 84R |

UNITED STATES PATENT AND TRADEMARK OFFICE
CERTIFICATE OF CORRECTION

PATENT NO. : 5,520,625

DATED : MAY 28, 1996

INVENTOR(S) : ANDRZEJ MALEWICZ

It is certified that error appears in the above-indentified patent and that said Letters Patent is hereby corrected as shown below:

| BM | 5,000,169 | 03/91 | SWICEGOOD ET AL. | 602 | 26 |
| BN | 5,002,044 | 03/91 | CARTER | 128 | 77 |
| BO | 5,002,045 | 03/91 | SPADEMAN | 128 | 80C |
| BP | 5,025,782 | 01/91 | SALERNO | 602 | 26 |
| BQ | 5,036,837 | 08/91 | MITCHELL ET AL. | 602 | 26 |
| BR | 5,060,640 | 10/91 | RASMUSSON | 128 | 80 |
| BS | 5,063,917 | 11/91 | YOUNG ET AL. | 602 | 26 |
| BT | 5,167,612 | 12/92 | BONUTTI | 602 | 20 |
| BU | 5,242,379 | 09/93 | HARRIS ET AL. | 602 | 26 |
| BV | 5,352,190 | 10/94 | FISCHER ET AL. | 602 | 26 |

FOREIGN PATENT DOCUMENTS

| BW | 1426-528-A | 09/88 | SU | 602 | 20 |

Col. 1, line 28, delete "twists", insert --wrists--

Col. 1, line 58, delete 'splits", insert --splints--

Col. 2, line 26, delete "split", insert --splint--

Col. 2, line 46, delete "split", insert --splint--

Col. 4, line 5, delete "Shall", insert --Shaft--

Col. 4, line 23, delete "shorn", insert --shown--

Signed and Sealed this

Twenty-first Day of January, 1997

Attest:

BRUCE LEHMAN

*Attesting Officer*   *Commissioner of Patents and Trademarks*